United States Patent [19]

Chadwick et al.

[11] Patent Number: 4,985,580
[45] Date of Patent: Jan. 15, 1991

[54] ALKYLATION OF SILANES

[75] Inventors: Kirk M. Chadwick, Hanover; Roland L. Halm, Madison, both of Ind.

[73] Assignee: Dow Corning Corporation, Midland, Mich.

[21] Appl. No.: 491,806

[22] Filed: Mar. 12, 1990

[51] Int. Cl.$^5$ .............................................. C07F 7/08
[52] U.S. Cl. ..................................................... 556/481
[58] Field of Search ......................................... 556/481

[56] References Cited

U.S. PATENT DOCUMENTS

| | | | |
|---|---|---|---|
| 2,403,370 | 7/1946 | Hurd | 556/481 |
| 2,598,436 | 5/1952 | Mohler et al. | 556/481 |
| 2,902,504 | 9/1959 | Nitzsche et al. | 556/481 |
| 3,065,253 | 11/1962 | Merritt | 556/481 X |
| 3,231,594 | 11/1962 | Merritt | 556/481 X |
| 4,155,927 | 5/1979 | Straussberger | 556/481 |
| 4,196,139 | 4/1980 | Seiler et al. | 556/481 X |
| 4,474,976 | 10/1984 | Faltynek | 556/481 |

OTHER PUBLICATIONS

Hurd, J. Am. Chem. Soc. (1945), 67: 1545-1548.
U.S. patent application Ser. Nos. 07/432,005 and 07/439,073, both filed Nov. 1989 by Chadwick.

*Primary Examiner*—Paul F. Shaver
*Attorney, Agent, or Firm*—William F. Boley

[57] ABSTRACT

The instant invention is a process for the addition of alkyl groups to non-halogen containing silanes. Non-halogen containing silanes are reacted with an alkyl halide in presence of a halogen-accepting metal. The process is run with or without a catalyst, which is effective in improving exchange of alkyl groups from the alkyl halide with hydrogen atoms of the silane.

32 Claims, No Drawings

ALKYLATION OF SILANES

BACKGROUND OF THE INVENTION

This invention relates to the addition of alkyl groups to non-halogen containing silanes to produce more highly alkylated silanes. More particularly, this invention relates to a process for reacting silanes with alkyl halides in the presence of a halide-accepting metal with or without the presence of a catalyst. The process, as described, can convert silanes to more valuable intermediates and to organosilanes which are easier to handle.

As an early example of the preparation of organosilicon compounds using metallic reagents, Kippling and Dilthey both demonstrated the alkylation of tetrachlorosilane by reaction with an organomagnesium halide, the well-known Grignard process.

Hurd, *J. Am. Chem. Soc.* (1945), Vol. 67, pp. 1545–1548, and Hurd, U.S. Pat. No. 2,403,370, issued July 2, 1946, disclose the alkylation of tetrachlorosilane and various methylchlorosilanes by passing the vapors of these chlorosilanes together with an alkyl halide over finely divided aluminum, zinc, or other reactive metal at elevated temperatures, 300°–500° C. Hurd discloses that a reaction occurs under these conditions in which chlorine groups on the chlorosilane are replaced by alkyl groups.

Straussberger et al., U.S. Pat. No. 4,155,927, issued May 22, 1979, discloses a process for preparing trimethylchlorosilane which comprises reacting methyldichlorosilane with methyl chloride and metallic aluminum in the presence of a diatomite.

Chadwick et al., pending U.S. application No. 07/432,005, filed Nov. 6, 1989 discloses a process for reacting a halide of silicon with an alkyl halide in the presence of a halogen accepting metal such as aluminum or zinc and a catalyst.

Chadwick et al., pending U.S. application No. 07/439,073, filed Nov. 17, 1989, discloses a process for reacting a halogen-containing disilane with an alkyl halide in the presence of a halogen accepting metal such as aluminum or zinc and a catalyst.

The above cited references do not teach a process for alkylating a non-halogen containing silane by reaction with an alkyl halide and a halogen accepting metal with or without the presence of a catalyst.

SUMMARY OF THE INVENTION

The objective of the instant invention is to provide a process for the preparation of more highly alkylated silanes from the reaction of non-halogen containing silanes with an alkyl halide in the presence of a halogen-accepting metal. The process may be run with or without a catalyst which is effective in improving exchange of alkyl groups from the alkyl halide with hydrogen atoms of the silane. A further objective of the instant invention is providing a process in which the alkylation of a non-halogen containing silane is effected at an improved rate of production, or increased selectivity toward the more highly alkylated organosilanes, or a combination of both.

The materials effective as a catalyst of the instant invention are theorized to be materials which improve contact of the vapors of the reactant alkyl halide and non-halogen containing silane with the halogen-accepting metal by facilitating increased penetration or disruption of a metal oxide film or layer on the surface of the halogen-accepting metal. However, the instant invention is not limited by this theory.

DESCRIPTION OF THE INVENTION

In accordance with the instant invention, there is provided a process to increase the number of alkyl groups on silanes under conditions that will be delineated herein. What is described, is a process for preparing more highly alkylated silanes having the formula, $$R^1_a R_n SiH_{4-a-n}$$

where each $R^1$ is independently selected from a group consisting of alkyl and substituted alkyl; each R is independently selected from a group consisting of methyl, ethyl, and n-propyl; a=0, 2, or 3; n=1, 2, 3 or 4; and a+n=1, 2, 3, or 4; said process comprising:

(A) contacting a silane having the formula, $$R^1_a SiH_{4-a}$$

where $R^1$ and a are defined above; with an alkyl halide, having the formula, $$RX$$

where $R^1$ is defined above and X is a halogen atom, in the presence of a metal which serves as a halogen acceptor;

(B) reacting the silane with the alkyl halide in the presence of the metal at a temperature between 200° and 400° C. to form the more highly alkylated silane and a halide of the metal.

In addition, the substituent $R^1$ can be alkenyl, aryl, or alkylaryl groups alone or in combination with alkyl and substituted alkyl groups. However, as will be disclosed herein, the process conditions are somewhat different than when $R^1$ consists exclusively of independently selected alkyl, and substituted alkyl groups.

The silanes which can be enriched in alkyl groups are silicon hydrides represented by the formula, $$R^1_a SiH_{4-a},$$

where a is 0, 1, 2, or 3. Each $R^1$ can be an alkyl group, for example, a hydrocarbon group containing 1 to 10 carbon atoms; a substituted alkyl group, for example, chloromethyl or trifluoropropyl; an alkenyl group, for example vinyl, allyl, or hexenyl. In addition, each $R^1$ can be an aryl or alkyaryl group, for example, phenyl, tolyl, or benzyl.

The silane can be, for example, silane ($SiH_4$), methylsilane, dimethylsilane, trimethylsilane, ethylsilane, diethylsilane, triethylsilane, methylethylsilane, dimethylethylsilane, methylpropylsilane, vinylsilane, methylvinylsilane, allylsilane, 3,3,3-trifluoropropylsilane, methyl(3,3,3-trifluoropropyl)silane, phenylsilane, diphenylsilane, methylphenylsilane, benzylsilane, or tolylsilane.

The alkyl halide can be, for example, methyl fluoride, methyl bromide, methyl chloride, ethyl fluoride, ethyl bromide, ethyl chloride, n-propyl fluoride, n-propyl bromide, or n-propyl chloride. Methyl chloride and ethyl chloride are preferred alkyl halides.

The molar ratio of the alkyl halide and the silane fed to the reactor can vary depending upon the starting reactants, the desired product, and the reaction conditions. Examples of molar ratios that are utilized are illustrated in the examples. A preferred molar ratio is 0.3 to 3 moles of alkyl halide per mole of hydrogen present on the silane.

The silane and the alkyl halide are contacted in the presence of a metal which serves as a halogen acceptor. In addition a catalyst may be present which facilitates the substitution of an alkyl group for a hydrogen of the silane.

The metal which serves as a halogen acceptor can be aluminum or zinc. The preferred metal is aluminum. The metal can be in the physical form, for example, of powders, wire, flake, granules, and chunks. It is preferred that the form of the metal expose as much surface area as possible to facilitate contact with the silane and the alkyl halide.

A catalyst may be employed which facilitates substitution of the R group of the alkyl halide for a hydrogen atom on the silane to yield more highly alkylated silanes. The catalyst is a material that provides the benefits, individually or in combination, of (1) shortened induction time to reach steady-state alkylation conditions; (2) increased conversion of the reactant hydrides of silicon and alkyl halide; and (3) increased overall incorporation of alkyl groups generated from the reacted alkyl halides into the silane. As an example, as shown in Example 2 infra, in the reaction of methyl chloride with trimethylsilane in the presence of aluminum about 0.84 moles of methyl are added per mole of Si. Addition of a catalyst such as tin metal at a concentration of 4200 ppm based upon the weight of the aluminum raises methyl incorporation to about 0.95 moles per mole of Si at the same conditions of temperature and contact time.

It is known in the art, that certain compounds attack aluminum. Examples of these compounds are hydrogen chloride, magnesium chloride, zinc chloride, phosphorous, and ferric chloride. It is theorized that catalysts that are effective at increasing alkyl/hydrogen exchange in the above reaction are those materials that improve contact of the vapors of the reactant alkyl halide and silane with the halogen-accepting metal by facilitating increased penetration or disruption of a metal oxide film or layer on the surface of the halogen-accepting metal. However, the instant invention is not limited by this theory.

The catalyst can include, for example tin metal and tin compounds, antimony and antimony compounds, magnesium and magnesium compounds, copper and copper compounds, mercury and mercury compounds, aluminum bromide, boron, phosphorous, metal phosphorous alloys, metal phosphides, palladium, iodine, iron chloride, hydrogen halides, and mixtures thereof. In considering aluminum as the halogen-accepting metal, the catalyst can further include zinc and zinc compounds. It is understood, that the term "compounds" includes both inorganic and organic compounds of the associated metals.

The catalyst is not limited to these materials or compounds used as examples. Any material or compound which functions in an equivalent manner to improve contact of the vapors of the reactant alkyl halide and the silane with the halogen-accepting metal by facilitating increased penetration or disruption of a metal oxide film or layer on the surface of the halogen-accepting metal is intended to be encompassed by the instant invention. The preferred catalysts are tin and tin compounds. The most preferred catalysts are tin metal and tin phosphide.

A sufficient quantity of catalyst varies with the particular catalyst. However, most catalysts are effective at concentrations of greater than about 3000 parts per million (ppm) by weight, based upon the weight of the halogen accepting metal. The inventors project that levels of catalyst of 100 ppm or greater are effective in increasing alkyl/hydrogen exchange. However, these lower amounts of catalyst are susceptible to inactivation and poisoning by impurities within the process. Levels of catalysts greater than about 3 percent by weight, based upon the weight of the halogen accepting metal, are effective and appear to have no detrimental effect. The inventors project that higher levels of catalysts can be utilized, but no additional benefit is anticipated.

When copper or copper compounds are used as a catalyst a preferred concentration is about 3,000 to 60.000 ppm. Higher concentrations of copper can be employed, but no advantage is perceived. Lower concentrations of copper may also work, but with reduced efficiency of alkyl/hydrogen exchange. The catalytic activity of copper and copper compounds may be improved by the presence of tin, tin compounds, zinc, zinc compounds, and mixtures thereof. A preferred concentration is about 50 to 3000 ppm zinc and/or tin.

The catalyst may be combined with the metal which serves as a halogen acceptor as a heterogeneous mixture of solids. The catalyst may also be combined as an alloy with the halogen accepting metal. The catalyst can be in the physical form, for example, of powders, granules, flakes, chips, or pellets.

The contact of the silane and the alkyl halide with the metal which serves as a halogen acceptor with or without catalyst can be effected by known means for gas-solid contact. Such contact can be effected by vaporizing the silane and the alkyl halide and feeding these vapors combined or separately to a vessel containing the solid metal with or without the catalyst. The solids can be configured in such contact arrangements as a packed bed, a stirred bed, a vibrating bed, or a fluidized bed.

To facilitate reaction of the hydride of silicon, the alkyl halide, and the metal with or without catalyst, a vessel having provisions to control the temperature of the contact zone is employed. For continuous operation, the vessel should include provisions to replenish the halogen-accepting metal as it is converted to metal halide.

The temperature in the contact zone to effect reaction should be about 200° to 400° C. for silanes that do not contain alkenyl, aryl, and alkylaryl substituents. Preferred is a range of about 300°–375° C. When the silane contains alkenyl, aryl, and alkylaryl substituents a temperature of 400°–500° C. is required. A preferred temperature range for silanes containing alkenyl, aryl, and alkylaryl substituents is considered to be 425°–475° C. Temperatures in excess of 500° C. are not desirable since the rate of cleavage of organic groups from silicon can be significant at these higher temperatures. Additionally, the rate of decomposition of alkyl halides at higher temperatures is also increased. Little reaction is projected to take place at temperatures less than the minimum values specified.

Residence time of the gaseous silane and the alkyl halide in contact with the halogen-accepting metal, with or without the catalyst, should be greater than about 0.5 seconds. It is preferred that residence time be in a range from about 1 to 15 seconds for silanes that do not contain alkenyl, aryl, or alkylaryl substituents. For silanes containing alkenyl, aryl, or alkylaryl substituents a preferred residence time is in a range from about 10 seconds to one hour.

The more highly alkylated silanes are separated and isolated from formed metal halide, unreacted silane, and unreacted alkyl halide. The metal halide can be a vapor or liquid at the conditions of the reaction. Separating the metal halide from the more highly alkylated silanes and remaining reactants can be effected by such known methods as cooling the stream exiting the contact vessel to a temperature low enough to allow recovery of the metal halide as a solid or liquid while passing the product silanes and remaining reactants through as a vapor. The metal halides can also remain in the reactor. The vapor stream of gaseous product, more highly alkylated silanes, and remaining reactants can be condensed to a liquid crude product. The more highly alkylated silanes can be isolated in high purity from the remaining reactants by such known methods as distillation.

So that those skilled in the art may better understand and appreciate the instant invention, the following examples are presented. These examples are presented to be illustrative and are not to be construed as limiting the claims as delineated herein.

EXAMPLE 1

An apparatus was assembled for the alkylation of silanes via the reaction of a silane with an alkyl halide in the presence of aluminum metal. This apparatus is typical of that used throughout the subsequent examples.

A carbon steel cylinder approximately 0.75 inch in diameter and capable of being loaded to a height of about 6 inches with solids was filled with aluminum metal mixed with tin metal catalyst. The cylinder was placed in an electrically heated fluidized sand bath to control the temperature of the cylinder and its contents. Feed of reactants to the cylinder were from the top of the cylinder to the bottom. The aluminum solids were held in place by a plug of glass wool.

Methyl chloride (MeCl) was fed as a gas from a compressed gas cylinder. Methyl chloride flow was controlled by a mass flow meter. The silane feed, in this case trimethylsilane (Me$_3$), was fed as a gas from a compressed gas cylinder. The MeCl and silane feeds were passed through approximately 4 feet of coiled stainless steel tubing in the heated fluidized sand bath.

The vapors exiting the reactor passed through a heated trap, temperature controlled at approximately 100° C., to remove AlCl$_3$ from the vapor stream as a solid. The remaining vapors were passed to a cold trap to recover the unreacted MeCl and the resultant methyl silanes mixture. The liquid crude product was then analyzed by gas chromatography (GC).

The reactor cylinder was charged with 16.1 g of aluminum powder. The aluminum powder was Alcan 44, atomized aluminum powder, purchased from Alcan-Toyo American, Joliet, Ill. The aluminum powder was mixed with approximately 5000 ppm of tin metal. The tin metal was a fine powder of less than about 325 mesh, purchased from Belmont Metals. The volume of the reactor filled with the aluminum and tin mixture was 10.4 cc. The reactor was heated to a furnace temperature of about 250° C. or 350° C. under a nitrogen purge. Trimethylsilane and MeCl gas were fed to the vaporizer and reactor at rates resulting in MeCl:Si mole ratios of 1.4, 1.5, and 2.6. At the reactor temperature, the reactant gases were calculated to have superficial velocities between 0.02 to 0.07 ft/s, with a residence time of 2 to 15 seconds.

A sample of the crude product was taken and analyzed by GC. Table 1 is a summary of these results. The samples are designated in Table 1 as "sample." The reaction temperature is designated as "°C." The molar feed ratio of methyl chloride to trimethylsilane is designated as "molar feed ratio MeCl:Si." The results of crude product analysis is represented by the percent of tetramethylsilane (%Me$_4$) and trimethylchlorosilane (%Me$_3$SiCl) content on a MeCl/Me$_3$ free basis. The percent of trimethylsilane converted to product is designated "%Si Conv." The term "ADME" is a measure of the additional Si-Me ligands created per mole of Si fed.

TABLE 1

| Tin Catalyzed Reaction of Trimethylsilane with Methyl Chloride and Aluminum. | | | | | |
|---|---|---|---|---|---|
| Sample | °C. | molar feed ratio MeCl:Si | ADME | % Si Conv. | % Me$_4$ | % Me$_3$Cl |
| A | 250 | 1.42 | 0 | 0 | 0 | 0 |
| B | 250 | 1.51 | 0 | 0 | 0 | 0 |
| C | 350 | 2.58 | .945 | 100 | 87.8 | 2.7 |

It is felt, that with a high enough residence time the reaction could be initiated at temperatures as low as 200° C.

EXAMPLE 2

Using the apparatus, procedures, and raw materials of Example 1, a comparison run (run D), without catalyst, was made to evaluate the effect of tin catalyst on the methylation of trimethylsilane in the presence of methyl chloride and aluminum metal. The results of this run are presented with the results of run C, with catalyst, for comparison. The specifics of run C are presented in Example 1. The results are presented in Table 2. The headings of Table 2 are the same as those for Table 1, with the addition of the term "Cat." which refers to the catalyst employed in the process.

TABLE 2

| Effect of Tin Catalyst on Methylation of Trimethylsilane by Methyl Chloride and Aluminum. | | | | | | |
|---|---|---|---|---|---|---|
| Sample | °C. | molar feed ratio MeCl:Si | Cat. | ADME | % Si Conv. | % Me$_4$ | % Me$_3$Cl |
| C | 350 | 2.58 | Sn | .945 | 100 | 87.8 | 2.7 |
| D | 350 | 2.15 | — | .835 | 91.5 | 83.6 | 7.9 |

These results indicate that the process can be run with or without the addition of catalyst. The beneficial effect of the catalyst is evidenced by the increased value of ADME.

EXAMPLE 3

Using the apparatus and procedures of Example 1, a run was made to evaluate the methylation of silane (SiH$_4$). The feed materials were silane and methyl chloride. The metal was aluminum powder and the catalyst was tin, both as previously described in Example 1. The results are presented in Table 3. The headings of Table 3 are the same as those of Table 1 with the exception that "%Me$_4$," "%Me$_3$SiH," and "%Me$_2$SiH$_2$" are the product distributions on a MeCl/SiH$_4$ free basis.

TABLE 3

Methylation of Silane by Reaction With Methyl Chloride and Aluminium in The Presence of Tin Catalyst.

| Sample | °C. | molar feed ratio MeCl:Si | ADME | % Si Conv. | % Me$_4$ | % Me$_3$SiH | % Me$_2$SiH$_2$ |
|---|---|---|---|---|---|---|---|
| E | 300 | 1.57 | 1.13 | NA[a] | 34 | 62 | 2.1 |
| F | 350 | 1.75 | 1.71 | 42 | 28 | 67 | 2.0 |

[a]Data not available

The data presented in Table 3 demonstrate the ability to methylate silane by the described process.

What is claimed is:

1. A process for preparing more highly alkylated silanes having the formula, $$R^1{}_aR_nSiH_{4-a-n}$$

where each $R^1$ is independently selected from a group consisting of alkyl and substituted alkyl; each R is independently selected from a group consisting of methyl, ethyl, and n-propyl; a=0, 1, 2, or 3; n=1, 2, 3, or 4; and a+n=1, 2, 3, or 4; said process comprising:

(A) contacting a silane having the formula, $$R^1{}_aSiH_{4-a}$$

where $R^1$ and a are defined above; with an alkyl halide, having the formula, $$RX$$

where R is defined above and X is a halogen atom, in the presence of a metal which serves as a halogen acceptor;

(B) reacting the silane with the alkyl halide in the presence of the metal at a temperature between 200° and 400° C. to form the more highly alkylated silane and a halide of the metal.

2. A process according to claim 1, where each R is independently selected from a group consisting of methyl and ethyl.

3. A process according to claim 1, where the temperature is 300°-375° C.

4. A process according to claim 1, where a sufficient quantity of a catalyst effective in improving exchange of the R groups from the alkyl halide with hydrogen atoms of the silane is employed.

5. A process according to claim 4, where the catalyst is a material that improves contact of the vapors of the reactant alkyl halide and the silane with the halogen-accepting metal by facilitating increased penetration or disruption of a metal oxide layer on the surface of the metal which serves as a halogen acceptor.

6. A process according to claim 5, where the catalyst is present as a discrete mixture With the halogen-accepting metal.

7. A process according to claim 5, where the catalyst is present as an alloy with the halogen-accepting metal.

8. A process according to claim 5, wherein the metal which serves as a halogen acceptor is aluminum.

9. A process according to claim 8, where the catalyst is selected from a group consisting of tin and tin compounds, zinc and zinc compounds, antimony and antimony compounds, copper and copper compounds, mercury and mercury compounds, magnesium and magnesium compounds, aluminum bromide, iron halides, boron, phosphorous, metal phosphorous alloys, metal phosphides, palladium, iodine, hydrogen halides, and mixtures thereof.

10. A process according to claim 9, where the catalyst is selected from a group consisting of tin metal and tin compounds.

11. A process according to claim 10, where the catalyst is selected from a group consisting of tin metal and tin phosphide.

12. A process according to claim 5, wherein the metal which serves as a halogen acceptor is zinc.

13. A process according to claim 12, where the catalyst is selected from a group consisting of tin and tin compounds, antimony and antimony compounds, copper and copper compounds, mercury and mercury compounds, magnesium and magnesium compounds, aluminum bromide, iron halides, boron, phosphorous, metal phosphorous alloys, metal phosphides, palladium, iodine, hydrogen halides, and mixtures thereof.

14. A process according to claim 13, where the catalyst is selected from a group consisting of tin metal and tin compounds.

15. A process according to claim 14, where the catalyst is selected from a group consisting of tin metal and tin phosphide.

16. A process for preparing more highly alkylated silanes having the formula, $$R^1{}_aR_nSiH_{4-a-n};$$

where each $R^1$ is independently selected from a group consisting of alkyl, substituted alkyl, alkenyl, aryl, and alkaryl groups; each R is independently selected from a group consisting of methyl, ethyl, and n-propyl; a=0, 1, 2, or 3; n=1, 2, 3, or 4., and a+n=1, 2, 3, or 4; said process comprising:

(A) contacting a silane having the formula, $$R^1{}_aSiH_{4-a};$$

where $R^1$ and a are defined above; with an alkyl halide, having the formula, $$RX$$

where R is defined above and X is a halogen atom, in the presence of a metal which serves as a halogen acceptor;

(B) reacting the silane with the alkyl halide in the presence of the metal at a temperature between 400° and 500° C. to form the more highly alkylated silanes and a halide of the metal.

17. A process according to claim 16, where each R is independently selected from a group consisting of methyl and ethyl.

18. A process according to claim 16, where the temperature is 425°-475° C.

19. A process according to claim 16, where a sufficient quantity of a catalyst effective in improving exchange of the R groups from the alkyl halide with hydrogen atoms of the silane is employed.

20. A process according to claim 19, where the catalyst is a material that improves contact of the vapors of the reactant alkyl halide and the silane with the halogen-accepting metal by facilitating increased penetration or disruption of a metal oxide layer on the surface of the metal which serves as a halogen acceptor.

21. A process according to claim 20, where the catalyst is present as a discrete mixture with the halogen-accepting metal.

22. A process according to claim 20, where the catalyst is present as an alloy with the halogen-accepting metal.

23. A process according to claim 20, where the metal which serves as a halogen acceptor is aluminum.

24. A process according to claim 23, where the catalyst is selected from a group consisting of tin and tin compounds, zinc and zinc compounds, antimony and antimony compounds, copper and copper compounds, mercury and mercury compounds, magnesium and magnesium compounds, aluminum bromide, iron halides, boron, phosphorous, metal phosphorous alloys, metal phosphides, palladium, iodine, hydrogen halides, and mixtures thereof.

25. A process according to claim 24, where the catalyst is selected from a group consisting of tin metal and tin compounds.

26. A process according to claim 25, where the catalyst is selected from a group consisting of tin metal and tin phosphide.

27. A process according to claim 20 where the metal which serves as a halogen acceptor is zinc.

28. A process according to claim 27, where the catalyst is selected from a group consisting of tin and tin compounds, antimony and antimony compounds, copper and copper compounds, mercury and mercury compounds, magnesium and magnesium compounds, aluminum bromide, iron halides, boron, phosphorous, metal phosphorous alloys, metal phosphides, palladium, iodine, hydrogen halides, and mixtures thereof.

29. A process according to claim 28, where the catalyst is selected from a group consisting of tin metal and tin compounds.

30. A process according to claim 29, where the catalyst is selected from a group consisting of tin metal and tin phosphide.

31. A process according to claim 1, where the silane is selected from a group consisting of $SiH_4$, methylsilane, dimethylsilane, and trimethylsilane; the alkyl halide is methyl chloride; the metal is aluminum; and the temperature is 300° to 375° C.

32. A process according to claim 5, where the catalyst is tin metal; the silane is selected from a group consisting of $SiH_4$, methylsilane, dimethylsilane, and trimethylsilane; the alkyl halide is methyl chloride; the metal is aluminum; and the temperature is 300° to 375° C.

* * * * *